United States Patent [19]
Yamada et al.

[11] Patent Number: 5,335,066
[45] Date of Patent: Aug. 2, 1994

[54] MEASURING METHOD FOR ELLIPSOMETRIC PARAMETER AND ELLIPSOMETER

[75] Inventors: Takeo Yamada; Akira Kazama; Takahiko Oshige, all of Tokyo, Japan

[73] Assignee: NKK Corporation, Tokyo, Japan

[21] Appl. No.: 133,762

[22] Filed: Oct. 7, 1993

Related U.S. Application Data

[63] Continuation of Ser. No. 816,612, Dec. 31, 1991, abandoned.

[30] Foreign Application Priority Data

Aug. 29, 1991 [JP] Japan ................................. 3-217657
Oct. 11, 1991 [JP] Japan ................................. 3-263689
Nov. 29, 1991 [JP] Japan ................................. 3-315686

[51] Int. Cl.$^5$ ............................................. G01J 4/04
[52] U.S. Cl. ................................. 356/364; 356/367; 356/369
[58] Field of Search ............... 356/364, 365, 366, 367, 356/369

[56] References Cited

U.S. PATENT DOCUMENTS

| | | | |
|---|---|---|---|
| 3,556,662 | 1/1971 | Leverstein et al. | 356/365 |
| 4,850,711 | 7/1989 | Sano et al. | 356/369 |
| 4,872,758 | 10/1989 | Miyazaki et al. | 350/369 |
| 5,073,025 | 12/1991 | Brooks | 356/367 |
| 5,102,222 | 4/1992 | Berger et al. | 356/365 |

FOREIGN PATENT DOCUMENTS 57-166533 10/1982 Japan .
61-83924 4/1986 Japan .
62-293104 12/1987 Japan .
63-36105 2/1988 Japan .
64-28509 1/1989 Japan .

OTHER PUBLICATIONS

Dill et al. "Ellipsometry with Pulsed Tunable Laser Sources" *IBM Technical Disclosure Bulletin* vol. 19, No. 4, (Sep. 1976) pp. 1487-1489.
Extended Abstracts (The 52nd Autumn Meeting, 1991); The Japan Society of Applied Physics, No. 3, p. 844.
The Review of Scientific Instruments, vol. 42, No. 1, Jan. 1971, pp. 19-22.

*Primary Examiner*—Richard A. Rosenberger
*Attorney, Agent, or Firm*—Frishauf, Holtz, Goodman & Woodward

[57] ABSTRACT

Movable optical parts included in an ellipsometer are omitted to increase the measurement speed and maintain constant, high measurement precision in film thickness measurement processing. A beam is radiated from a light source section onto a measurement target. A reflected beam having an elliptically polarized beam reflected by the measurement target is divided into four light components polarized in different directions. The optical intensities of the respective polarized light components are detected. Of the four detected optical intensities, one having the minimum value is omitted, and ellipsometric parameters $\psi$ and $\Delta$ are calculated by using the remaining three optical intensities having the largest values. The ellipsometer comprises only stationary optical parts without using any movable optical parts. The polarization directions of the respective polarized light components, from which four optical intensities are obtained, are set at angles of 90°, 0°, +45°, and −45° with respect to a reference direction. A composite beam splitter is used to extract the four polarized light components.

10 Claims, 11 Drawing Sheets

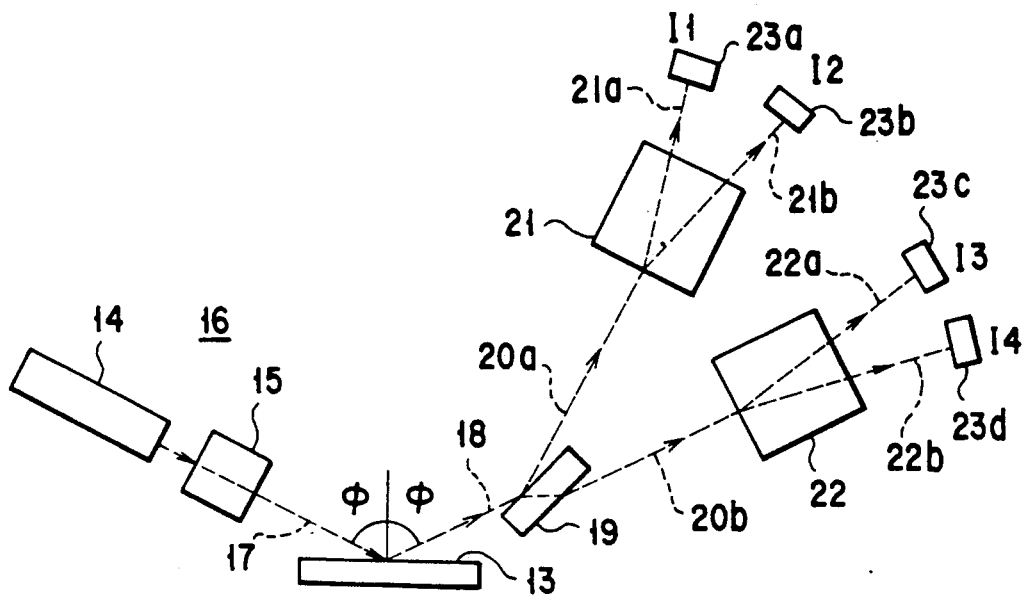
F I G. 1
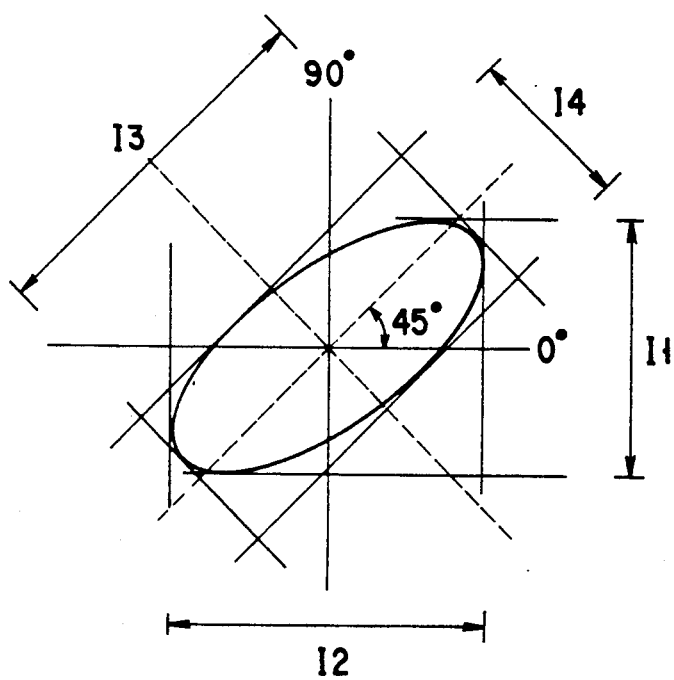
F I G. 2

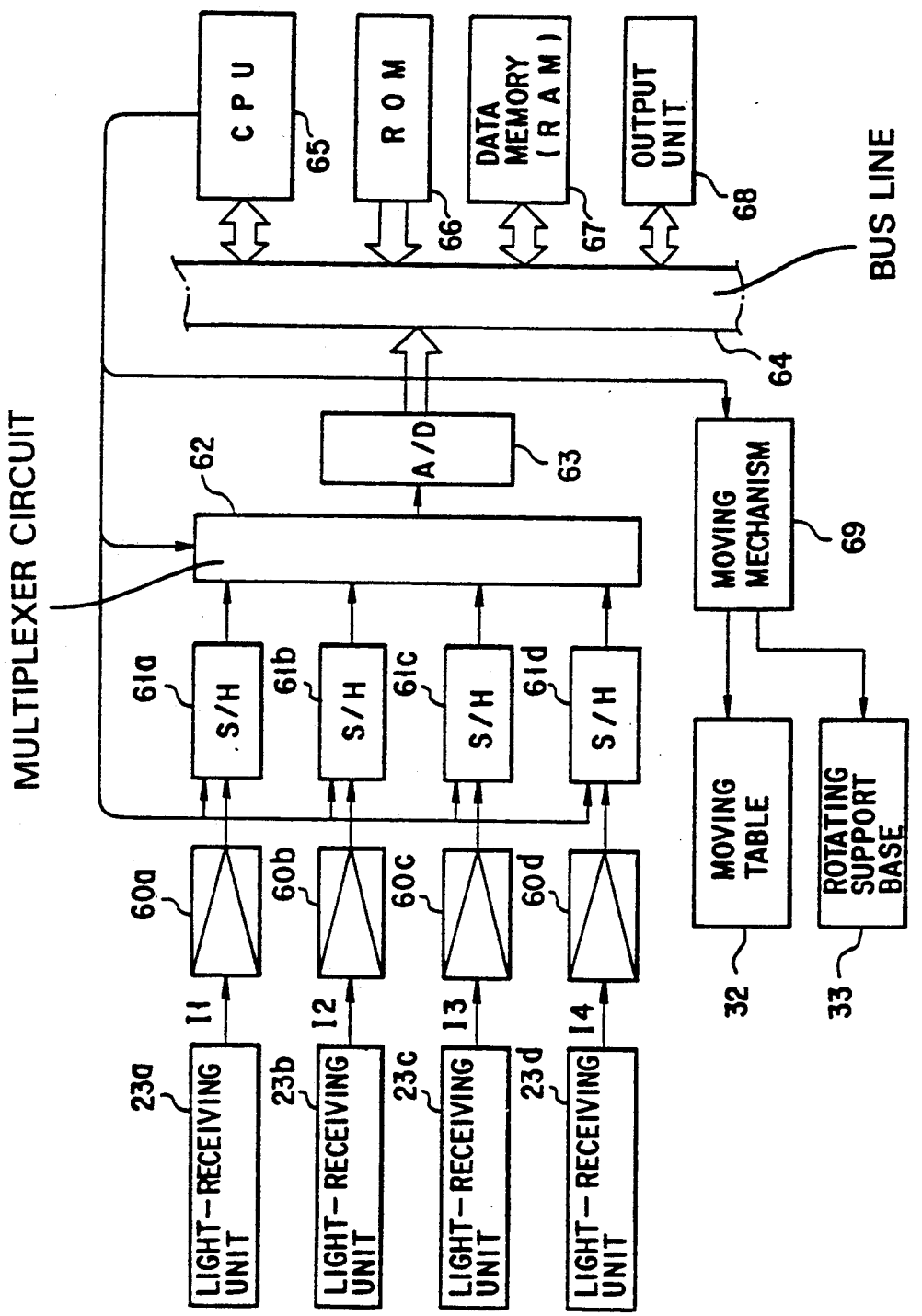
F I G. 7

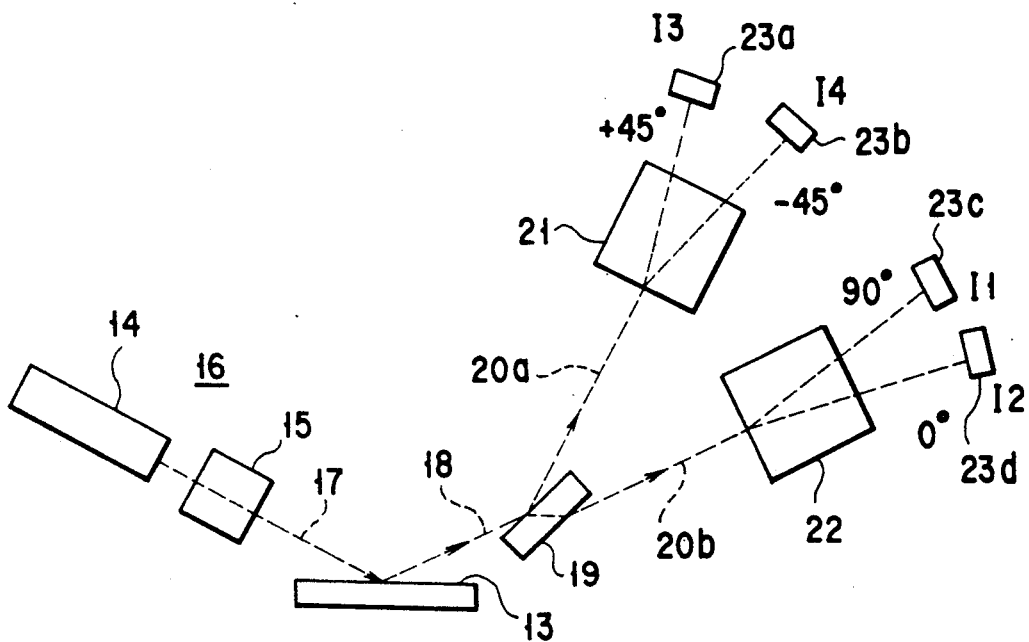
F I G. 9
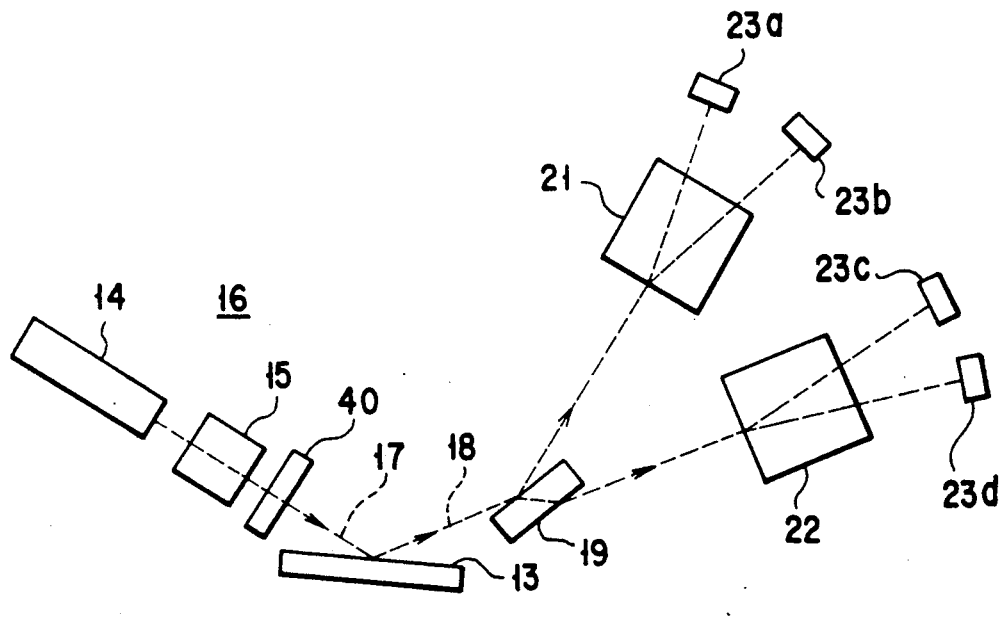
F I G. 10

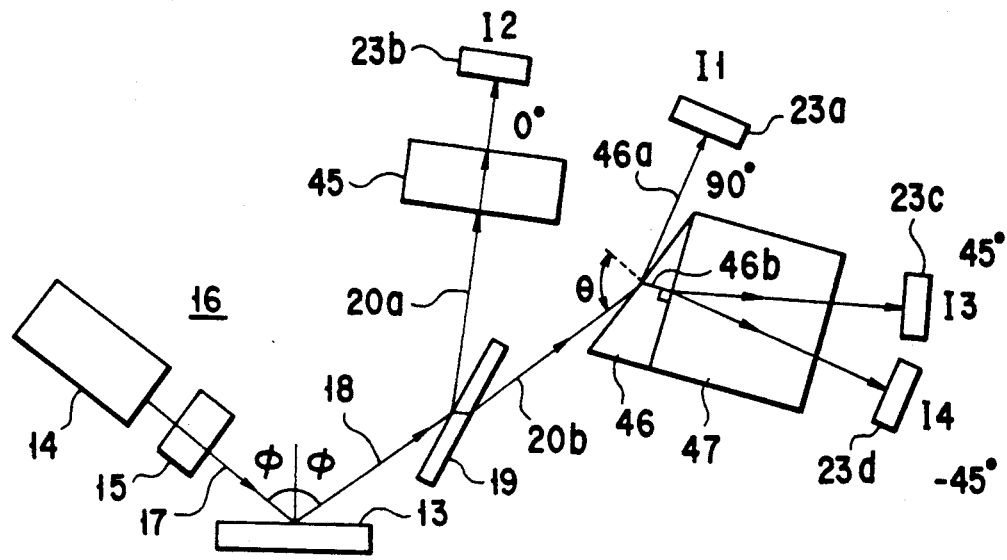
F I G. 14
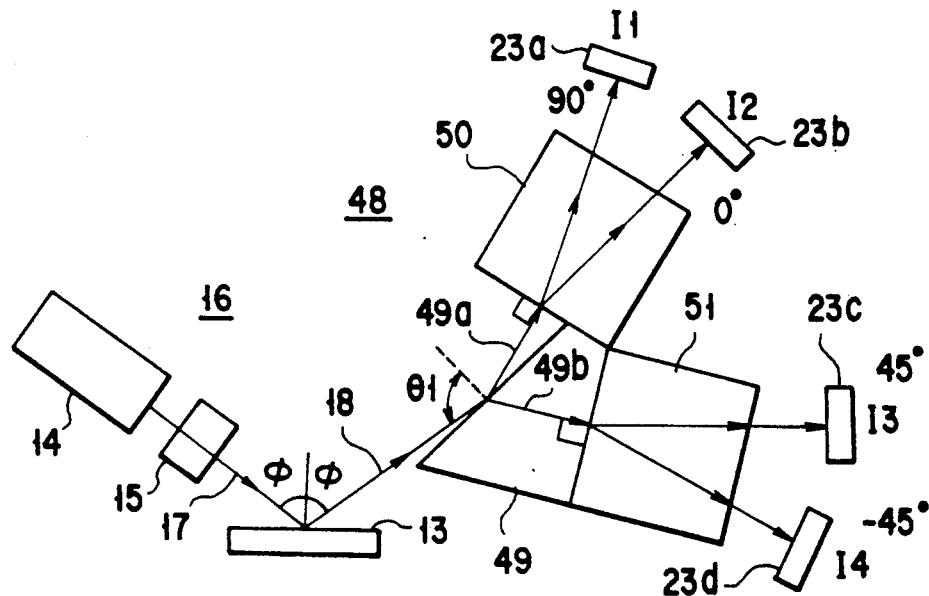
F I G. 15

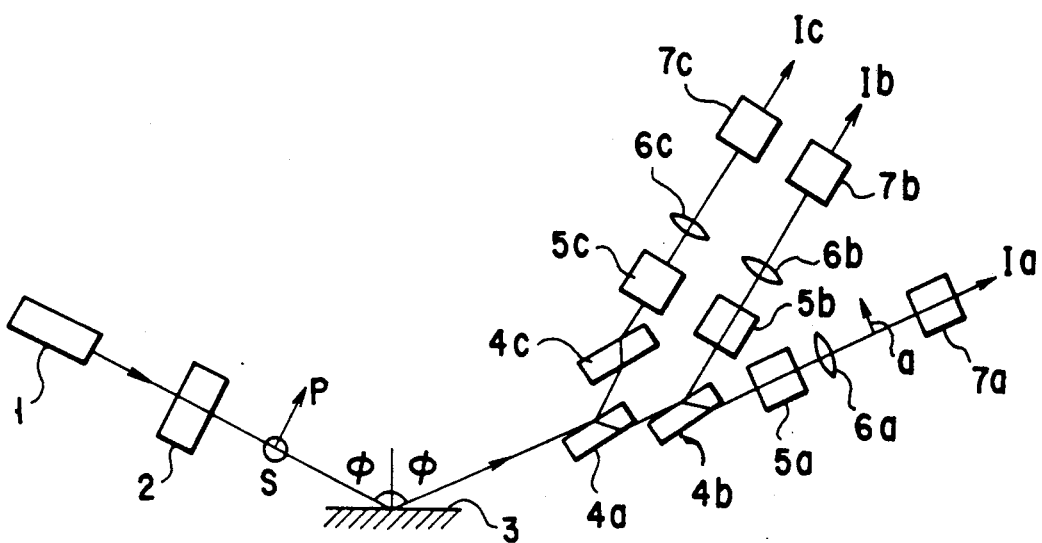
F I G. 18
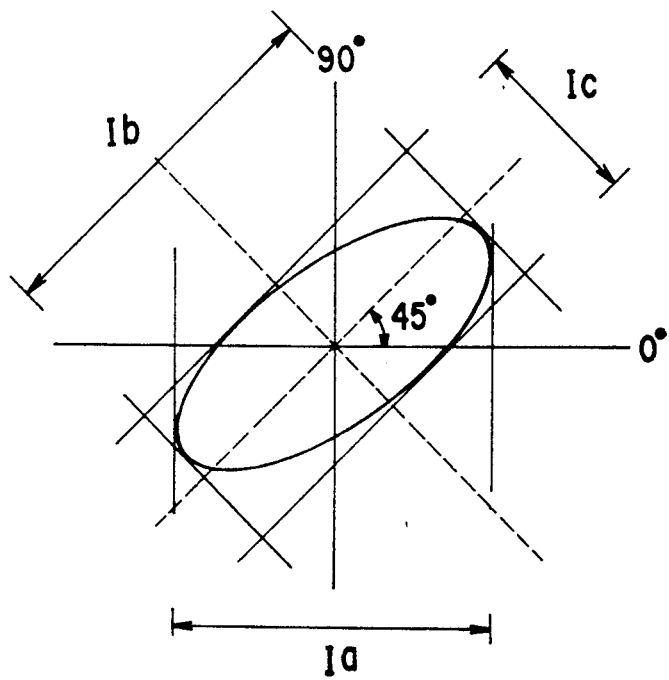
F I G. 19

MEASURING METHOD FOR ELLIPSOMETRIC PARAMETER AND ELLIPSOMETER

This application is a continuation of application Ser. No. 07/816,612, filed Dec. 31, 1991, now abandoned.

BACKGROUND OF THE INVENTION

The present invention relates to a method and apparatus for measuring ellipsometric parameters, which ellipsometric parameters are used to measure the thickness of a thin film accurately, and, more particularly, to a measuring method for ellipsometric parameters and an ellipsometer designed to select an optimal measurement condition automatically.

As a method of measuring the thickness of a thin film, ellipsometry is used. In this method, a change in polarization state upon reflection of a beam by a sample surface, i.e., a ratio $\rho$ between a reflectance Rp of a light component (P component) parallel to the incident plane of an electric field vector and a reflectance Rs of a light component (S component) perpendicular thereto, is measured according to equation (1), and a film thickness d is obtained in accordance with a predetermined relationship between the already obtained polarization reflectance ratio $\rho$ and the film thickness d:

$$\rho = Rp/Rs = \tan \psi \exp[j\Delta] \tag{1}$$

In this case, since the polarization reflectance ratio $\rho$ is represented by a complex number as indicated by equation (1), two ellipsometric parameters, i.e., an amplitude ratio $\psi$ and a phase difference $\Delta$, must be obtained.

As a conventional method of obtaining these ellipsometric parameters $\psi$ and $\Delta$, a rotating analyzer method is known. In this method, for example, a polarized beam is radiated from a light source onto a measurement target at a predetermined angle, and a reflected beam from the measurement target, which is elliptically polarized, is guided to a light-receiving unit through a rotating analyzer. Subsequently, the ellipsometric parameters are calculated on the basis of the optical intensity signal waveforms obtained by the light-receiving unit at this time.

However, in order to execute one measuring operation, the analyzer must be rotated once and the resulting optical intensity signals must be observed. This rotation requires a predetermined period of time or more. Therefore, it is impossible to measure a film thickness on a measurement target which is moving at high speed. In addition, the presence of a mechanical movable portion increases the size of the apparatus itself. For this reason, the apparatus cannot be installed on a production line in a factory to perform on-line measurement of measurement targets, e.g., continuously supplied measurement targets.

In order to eliminate such inconveniences, a 3-channel ellipsometer, in which movable parts are eliminated, (Published Unexamined Japanese Patent Application Nos. 63-36105 and 1-28509) has been developed, as shown in FIG. 18.

For example, a beam having a single wavelength, output from a light source 1 constituted by, a laser source, is linearly polarized by a polarizer 2 and is incident on a sample surface 3 as a measurement target at a predetermined angle $\phi$. Assume that, on the sample surface 3, an incident plane is parallel to the surface of the drawing, and that a direction parallel to the surface of the drawing is defined as a P direction; and a direction perpendicular to the surface of the drawing, an S direction. A reflected beam from the sample surface 3 is split into three beams by three non-polarizing beam splitters 4a, 4b, and 4c. Each of the beam splitters 4a to 4c is constituted by an optically isotropic, transparent member. In addition, the beam splitters 4a to 4c are fixed to be parallel to each other.

A first beam transmitted through the two beam splitters 4a and 4b is incident on a first light-receiving unit 7a through a first analyzer 5a and a condenser lens 6a. The first light-receiving unit 7a converts an optical intensity Ia of the beam into an electrical signal. Similarly, a second beam transmitted through the beam splitter 4a and reflected by the next beam splitter 4b is incident on a second light-receiving unit 7b through a second analyzer 5b and a condenser lens 6b. The second light-receiving unit 7b converts an optical intensity Ib of the beam into an electrical signal. In addition, a third beam reflected by the beam splitter 4a and transmitted through the next beam splitter 4c is incident on a third light-receiving unit 7c through a third analyzer 5c and a condenser lens 6c.

The third light-receiving unit 7c converts an optical intensity Ic of the beam into an electrical signal.

Each of the analyzers 5a to 5c serves as an element for checking the presence/absence of polarization and a polarization direction, and has the same constitution as that of the polarizer. Each of the analyzers 5a to 5c transmits only a light component which oscillates in a set direction. The polarization direction of the first analyzer 5a is set in a reference direction (an azimuth of 0°). The polarization direction of the second analyzer 5b is set to be inclined at an angle of +45° with respect to the reference direction. The polarization direction of the third analyzer 5c is set to be inclined at an angle of −45° with respect to the reference direction. Note that the reference direction is a direction in which a direction (P direction) parallel to the incident plane of a beam incident on the sample surface 3 is defined as an azimuth of 0°, when viewed from the direction of the light-receiving unit 7a, as indicated by an arrow a in FIG. 18.

If, therefore, the light reflected by the sample surface 3 is elliptically polarized, as shown in FIG. 19, the first optical intensity Ia obtained by the first light-receiving unit 7a represents the amplitude, of the elliptically polarized beam shown in FIG. 19, which is orthographically projected on the axis of abscissa (0° direction). The second optical intensity Ib obtained by the second light-receiving unit 7b represents the amplitude, of the elliptically polarized beam, which is orthographically projected on a line inclined at an angle of +45°. The third optical intensity Ic obtained by the third light-receiving unit 7c represents the amplitude, of the elliptically polarized beam, which is orthographically projected on a line inclined at an angle of −45°.

The above-mentioned ellipsometric parameters $\psi$ and $\Delta$ are the amplitude ratio $\psi$ and the phase difference $\Delta$ between the P and S components of the reflected beam from the sample surface 3, which is elliptically polarized, as shown in FIG. 19. Simple geometrical examination reveals that the ellipsometric parameters can be obtained according to equations (2) and (3):

$$\cos \Delta = (Ib - Ic)/(2Ia)\{Ia/(Ib + Ic - Ia)\}^{\frac{1}{2}} \tag{2}$$

$$\tan \psi = (\sigma 1 \cdot \sigma 2)\{Ia/(Ib+Ic-Ia)\}^{\frac{1}{2}} \quad (3)$$

Note that the amplitude reflectance ratio $\sigma 1$ and the amplitude transmittance ratio $\sigma 2$ in the direction of each of the beam splitters $4a$ to $4c$ are inherent values, which are obtained in advance by radiating a test beam having a known elliptically polarized beam onto each of the beam splitters $4a$ to $4c$.

When the ellipsometric parameters $\psi$ and $\Delta$ are obtained in this manner, the film thickness d is obtained by using another equation.

However, in the conventional ellipsometer shown in FIG. 18, the following problems are still posed.

The optical intensities detected by the light-receiving units $7a$ to $7c$ greatly change depending on the shape of the elliptically polarized beam of the reflected beam from the sample surface 3, as shown in FIG. 19. For example, as the elliptic shape shown in FIG. 19 becomes flatter, only the third optical intensity Ic is greatly reduced as compared with the other optical intensities Ia and Ib.

In order to calculate the above-mentioned ellipsometric parameters $\psi$ and $\Delta$ by, e.g., a computer, the optical intensities Ia to Ic must be converted into digital values by an A/D converter. If, therefore, only one optical intensity is small, the number of effective digits of the A/D-converted values is decreased, resulting in a large error. As a result, the precision of the calculated ellipsometric parameters $\psi$ and $\Delta$ decreases, and hence the measurement precision of the finally obtained film thickness d decreases.

When optical intensity Ia takes a value close to "0", both the numerator and denominator of the fraction at the right side of Equation (2) also take values, close to "0", thus decreasing the calculation accuracy.

As described above, although the 3-channel ellipsometer shown in FIG. 18 is a very useful apparatus for measuring a film thickness on a measurement target at high speed because it has no movable portions, its measurement precision may become lower than that of the above-described ellipsometer using the rotating analyzer depending on the type of measurement target.

Note that if the number of measuring operations at the same measurement point is increased, and the average of the measurement results is obtained, a reduction in error can be achieved to some extent. However, repetitive measurement of the same measurement point prolongs the overall measurement time and cannot be applied to a measurement target which moves at high speed in the process of, e.g., film thickness test in a production line in a factory.

The present invention has been made in consideration of the above situation, and has as its object to provide a measuring method for ellipsometric parameters and an ellipsometer, in which a reflected beam having an elliptically polarized beam reflected by a measurement target is divided into four different polarized light components, the optical intensities of the respective polarized light components are detected, and a low optical intensity of the detected optical intensities is omitted, thereby calculating ellipsometric parameters by using only high optical intensities, and achieving a great increase in film thickness measurement precision while maintaining a high measurement speed.

SUMMARY OF THE INVENTION

In order to achieve the above object, according to the present invention, there is provided a measuring method for ellipsometric parameters, in which a polarized beam is radiated on a measurement target at a predetermined angle, a reflected beam from the measurement target is divided into four different polarized light components, three high optical intensities of optical intensities of the four polarized light components are selected, and ellipsometric parameters are calculated on the basis of the three selected optical intensities.

In addition, according to the present invention, there is provided an ellipsometer comprising a light source section for radiating a polarized beam onto a measurement target at a predetermined angle, a non-polarizing beam splitter for splitting a reflected beam from the measurement target in two different directions, a plurality of optical members for dividing each beam, split by the non-polarizing beam splitter, in two different polarization directions, thus dividing the reflected beam, reflected by the measurement target, into four polarized light components, four light-receiving units for detecting optical intensities of the respective polarized light components divided by the plurality of optical members, and an arithmetic section for selecting three high optical intensities of the four optical intensities detected by the four light-receiving units and calculating ellipsometric parameters of an elliptically polarized beam of the reflected beam on the basis of the three selected optical intensities.

According to another aspect of the present invention, the plurality of optical members comprise a first optical system for dividing one of the beams, split by the non-polarizing beam splitter, into light components polarized in directions at $+90°$ and $0°$ with respect to a reference direction, and a second optical system for dividing the other beam, split by the non-polarizing beam splitter, into light components polarized in directions at $+45°$ and $-45°$ with respect to the reference direction.

Furthermore, a wave plate may be inserted in one of the optical paths of incident and reflected beams with respect to the measurement target.

According to still another aspect of the present invention, there is provided an ellipsometer comprising a light source section for radiating a polarized beam onto a measurement target at a predetermined angle, a composite beam splitter for splitting a reflected beam from the measurement target into four different polarized light components, four light-receiving units for detecting optical intensities of the respective polarized light components divided by the composite beam splitter, and an arithmetic section for selecting three high optical intensities of the four optical intensities detected by the four light-receiving units and calculating ellipsometric parameters of an elliptically polarized beam of the reflected beam on the basis of the three selected optical intensities.

According to still another aspect of the present invention, the composite beam splitter comprises a non-polarizing glass for splitting the reflected beam from the measurement target, at an incident surface of the non-polarizing glass, into a reflected beam and a transmitted beam, a first polarizing beam splitter, having one end fixed to the non-polarizing glass, for splitting the reflected beam from the non-polarizing glass into light components polarized in directions at $+90°$ and $0°$ with respect to a reference direction, and a second polarizing beam splitter, bonded to an exit surface of the non-polarizing glass, from which the transmitted beam emerges, for splitting the transmitted beam from the non-polarizing glass into light components polarized in directions at +45° and −45° with respect to the reference direction.

Furthermore, the first polarizing beam splitter is designed to divide a reflected beam into light components polarized in directions at +45° and −45° with respect to the reference direction, and the second polarizing beam splitter is designed to divide a reflected beam into light components polarized in directions at +90° and 0° with respect to the reference direction.

The operation principle of the measuring method for ellipsometric parameters, which has such an arrangement, will be described below. As described above, when a polarized beam from the light source section is incident on a measurement target at a predetermined angle $\phi$, a beam reflected by the measurement target has an elliptically polarized beam having a predetermined shape defined by the film thickness or the like on the measurement target. Since the ellipsometric parameters $\psi$ and $\Delta$ are the amplitude ratio $\psi$ and the phase difference $\Delta$ between the P and S components of the reflected beam from the measurement target, the ellipsometric parameters can be obtained from the shape of the ellipse and the degree of inclination of the ellipse from a reference line. Therefore, as shown in FIG. 19, if at least three optical intensities are obtained by projecting the ellipse in the respective directions, the ellipse can be uniquely determined. Consequently, as shown in, e.g., FIG. 2, even if projected data in four directions are obtained, and one of them is omitted to obtain the remaining three projected data, the ellipse can be uniquely determined.

Therefore, in the measuring method for ellipsometric parameters and the ellipsometer of the present invention, a reflected beam having an elliptically polarized beam reflected by a measurement target is split in two directions by the non-polarizing beam splitter, and a beam in each direction is further divided into light components polarized in two directions. Thus, four light components polarized in different directions can be obtained, and converted into respective optical intensities. Since these four optical intensities are values obtained by projecting the above-described ellipse in different directions, the ellipsometric parameters $\psi$ and $\Delta$ can be obtained by using three optical intensities arbitrarily selected from the four optical intensities.

In this case, of the four optical intensities, one having the minimum value, which can be regraded as data including an error to the greatest degree, is omitted, and calculations are performed by using the three optical intensities having large values, thereby achieving an increase in precision of the calculated ellipsometric parameters $\psi$ and $\Delta$.

Calculations of the ellipsometric parameters $\psi$ and $\Delta$ can be simplified by setting the polarization directions of the respective polarized light components at 90°, 0°, +45°, and −45° with respect to the reference direction in which the incident plane of a beam incident on a measurement target is defined as an azimuth of 0° (P direction).

Furthermore, the reflected beam from the measurement target is divided into four different polarized light components by the composite beam splitter constituted by one optical member. By using the composite beam splitter, the number of optical parts can be reduced, and a compact, lightweight ellipsometer can be manufactured.

In addition, the composite beam splitter is constituted by the non-polarizing glass and the first and second polarizing beam splitters. In the composite beam splitter having such an arrangement, the reflected beam from the measurement target is divided into a transmitted beam and a reflected beam at the surface of the non-polarizing glass. The reflected beam is then divided into two light components polarized at +90° and 0° with respect to the reference direction by the second polarizing beam splitter. Similarly, the transmitted beam is divided into two light components polarized at +45° and −45° with respect to the reference direction by the second polarizing beam splitter. As a result, the reflected beam is divided into four different polarized light components.

Moreover, the reflected beam can be divided into light components polarized in directions at +45° and −45° by the first polarizing beam splitter, and the transmitted beam can be divided into light components polarized in directions at +90° and 0° by the second polarizing beam splitter.

BRIEF DESCRIPTION OF THE DRAWINGS

Embodiments of the present invention will be described below with reference to the accompanying drawings.

FIG. 1 is a view showing the internal structure of an ellipsometer main body according to an embodiment of the present invention.

FIG. 2 is a view showing the elliptically polarized beam of a reflected beam in the ellipsometer of the embodiment of FIG. 1.

FIG. 7 is a block diagram showing the electrical arrangement of the oxide film thickness measuring apparatus.

FIG. 9 is a view showing the internal structure of an ellipsometer main body according to another embodiment of the present invention.

FIG. 10 is a view showing the structure of an ellipsometer according to still another embodiment of the invention.

FIG. 14 is a view showing the structure of an ellipsometer according to still another embodiment of the invention.

FIG. 15 is a view showing the structure of an embodiment using a composite beam splitter.

FIG. 18 is a schematic view showing the arrangement of a conventional ellipsometer.

FIG. 19 is a view showing the elliptically polarized beam of a reflected beam in general.

DETAILED DESCRIPTION

Figure 3:
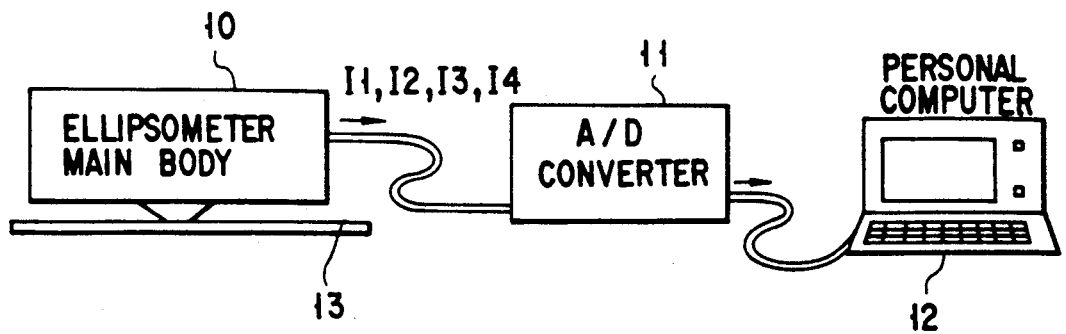
FIG. 3 is a schematic view showing the overall arrangement of the ellipsometer of the embodiment of FIG. 1.

FIG. 3 is a block diagram showing the overall ellipsometer using a measuring method for ellipsometric parameters according to an embodiment of the invention. Referring to FIG. 3, reference numeral 10 denotes an ellipsometer main body housed in a case made of a light metal material. Optical intensities I1, I2, I3, and I4 output from the ellipsometer main body 10 are converted into digital values by an A/D converter 11. The digital values are then input to a personal computer 12 serving as an arithmetic section. The personal computer 12 omits one of the input optical intensities I1, I2, I3, and I4, which has the minimum value, and calculates ellipsometric parameters $\psi$ and $\Delta$ by using the remaining three optical intensities. In addition, a film thickness d on a sample surface 13 as a measurement target is calculated on the basis of the calculated ellipsometric parameters $\psi$ and $\Delta$ by using predetermined equations.

In this case, the A/D converter 11 sequentially A/D-converts the optical intensities I1, I2, I3, and I4 in a time-divisional manner. Note that a conversion time per optical intensity is about 10 $\mu$sec. Therefore, a measurement time required to measure the ellipsometric parameters $\psi$ and $\Delta$ and the film thickness d at one measurement point sampled on the sample surface 13, including a calculation time in the personal computer 12, is about 100 $\mu$sec. Note that since the optical intensities I1, I2, I3, and I4 are simultaneously measured and held in a voltage holding circuit, even if the sample surface 13 moves at high speed, the above-described operation can be satisfactorily performed.

FIG. 1 shows the internal arrangement of the ellipsometer main body 10. A laser beam having a single wavelength, which is emitted from, e.g., a semiconductor laser source 14 is linearly polarized by a polarizer 15. That is, the semiconductor laser source 14 and the polarizer 15 constitute a light source section 16. An incident beam 17, which is linearly polarized, is radiated from the light source section 16 onto the sample surface 13 at an angle $\phi$. A reflected beam 18, reflected by the sample surface 13, is converted from the linearly polarized beam into an elliptically polarized beam shown in FIG. 2 because of the presence of a film on the sample surface 13, and is incident on a non-polarizing beam splitter 19.

The non-polarizing beam splitter 19 is constituted by, e.g., a non-polarizing glass plate. The incident beam 18, which is reflected is split into two beams 20a and 20b while the beam 18 is not polarized at all and its elliptical polarization state is held. The reflected beam 20a is incident on a first polarizing beam splitter 21. The transmitted beam 20b is incident on a second polarizing beam splitter 22.

The first and second polarizing beam splitters 21 and 22 have the same constitution. Each beam splitter comprises a Glan-Thompson prism, a Glan-Taylor prism, or the like and is designed to split an incident beam having an elliptically polarized beam into polarized light components in two orthogonal directions and to output them as transmitted and reflected beams, respectively. Note that each beam splitter may comprise a Wollaston prism or the like designed to split a transmitted beam into two components at a certain angle.

The first polarizing beam splitter 21 as the first optical system is positioned such that a transmitted beam 21a from the first polarizing beam splitter 21 is polarized counterclockwise at an angle of $+90°$ with respect to the above-mentioned reference direction in which the direction parallel to the incident plane of a light beam incident on the sample surface 13 is defined as an azimuth of $0°$, when viewed from the direction of a light-receiving unit 23a. The transmitted beam 21a output from the first polarizing beam splitter 21 and polarized at an angle of $+90°$, is incident on the light-receiving unit 23a. A reflected beam 21b output from the first polarizing beam splitter 21 and polarized at an angle of $0°$ is incident on a light-receiving unit 23b.

The second polarizing beam splitter 22 as the second optical system is positioned such that a transmitted beam 22a from the second polarizing beam splitter 22 is polarized at an angle of $+45°$ with respect to the reference direction. The transmitted beam 22a output from the second polarizing beam splitter 22 and polarized at an angle of $+45°$, is incident on a light-receiving unit 23c. A reflected beam 22b output from the second polarizing beam splitter 22 and polarized at an angle of $-45°$ is incident on a light-receiving unit 23d.

With this operation, the optical intensity I1 (first channel), of the elliptically polarized beam (shown in FIG. 2) of the reflected beam 18, which is projected on the axis of the ordinate is obtained on the basis of the transmitted beam 21a incident on the light-receiving unit 23a. The optical intensity I2 (second channel), of the elliptically polarized beam, which is projected on the axis of the abscissa is obtained on the basis of the reflected beam 21b incident on the light-receiving unit 23b. The optical intensity I3 (third channel), of the elliptically polarized beam, which is projected on a line inclined at an angle of $+45°$ with respect to the axis of abscissa is obtained on the basis of the transmitted beam 22a incident on the light-receiving unit 23c. In addition, the optical intensity I4 (fourth channel), of the elliptically polarized beam, which is projected on a line inclined at an angle of $-45°$ with respect to the axis of abscissa is obtained on the basis of the reflected beam 22b incident on the light-receiving unit 23d.

That is, the reflected beam 18 from the sample surface 13 is divided into polarized light components respectively having the optical intensities I1, I2, I3, and I4 and polarized in four directions at angles of $90°$, $0°$, $+45°$, and $-45°$.

As described above, the ellipsometric parameters $\psi$ and $\Delta$ defining the elliptically polarized beam are calculated by using the three highest optical intensities of these four optical intensities I1 to I4.

Condition A . . . the optical intensity I1 is minimum (calculations are performed by using the optical intensities I2, I3, and I4):

$$\tan \psi = \sigma 3 [2I2/\{(1+\sigma 3^2)(I3+I4)-2I2\}]^{\frac{1}{2}}$$

$$\cos \Delta = [(1+\sigma 3^2)(I3-I4)/4I2] \times [2I2/\{(1+\sigma 3^2)(I3 +I4)-2I2\}]^{\frac{1}{2}}$$

Note that the amplitude transmittance $\sigma 3$ of the non-polarizing beam splitter 19 is an inherent value. A test beam having a known linearly or elliptically polarized beam is radiated on the non-polarizing beam splitter 19, and this inherent value is obtained in advance on the basis of deviations from the true ellipsometric parameters $\psi$ and $\Delta$.

Condition B . . . the optical intensity I2 is minimum (calculations are performed by using the optical intensities I1, I3, and I4):

$$\tan \psi = [\{(1+\sigma 3^2)(I3+I4)-2\sigma 3^2 I1\}/2I1]^{\frac{1}{2}}$$

$$\cos \Delta = [(1+\sigma 3^2)(I3-I4)/4\sigma 3I1] \times [2I1/\{(1+\sigma 3^2)(I3+I4)-2\sigma 3^2 I1\}]^{\frac{1}{2}}$$

Condition C . . . the optical intensity I3 is minimum (calculations are performed by using the optical intensities I1, I2, and I4):

$$\tan \psi = (I2/I1)^{\frac{1}{2}}$$

$$\cos \Delta = -[(1+\sigma 3^2)I4-I2-\sigma 3^2 I1]/[2\sigma 3(I1\ I2)^{\frac{1}{2}}]$$

Condition D . . . the optical intensity I4 is minimum (calculations are performed by using the optical intensities I1, I2, and I3):

$$\tan \psi = (I2/I1)^{\frac{1}{2}}$$

$$\cos \Delta = [(1+\sigma 3^2)I3-I2-\sigma 3^2 I1]/[2\sigma 3(I1\ I2)^{\frac{1}{2}}]$$

Figure 4:
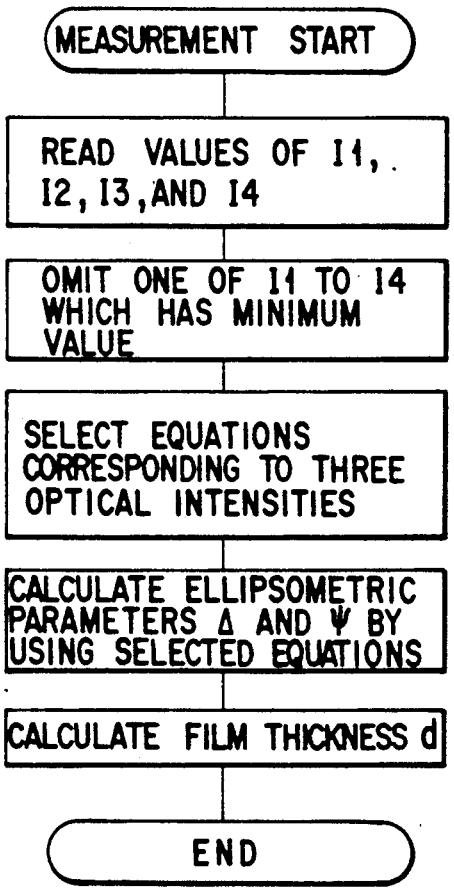
FIG. 4 is a flow chart showing an operation of the ellipsometer of the embodiment of FIG. 1.

The personal computer 12 as an arithmetic section calculates the film thickness d on the sample surface 13 on the basis of the four digital optical intensities I1 to I4 input from the ellipsometer main body 10 through the A/D converter 11 in accordance with the flow chart in FIG. 4.

In the first step of the flow chart, the four optical intensities I1 to I4 are read. In the next step, the minimum optical intensity of the four optical intensities is omitted. Of the conditions A to D, one with which the remaining optical intensities coincide is retrieved. Subsequently, the equations designated by the retrieved condition are selected, and the ellipsometric parameters $\psi$ and $\Delta$ are calculated by using the selected equations. When the ellipsometric parameters $\psi$ and $\Delta$ are obtained, the film thickness d on the sample surface 13 is calculated by using another equation.

In the ellipsometer having such an arrangement, of the four optical intensities I1 to I4, one having the minimum value, which is regarded as an optical intensity including an error to the highest degree, is omitted. Thereafter, the ellipsometric parameters $\psi$ and $\Delta$ are calculated by using the remaining three optical intensities which are regarded as data including errors to lower degrees. The condition where the numerator and denominator are close to "0" can be eliminated from the calculation. Therefore, the calculated ellipsometric parameters $\psi$ and $\Delta$ are improved in precision.

Since calculations are always performed by selecting optical intensities in an optimal condition, the measurement precision can be maintained at a level higher than a certain level all the time, as compared with the conventional 3-channel ellipsometer designed to calculate the ellipsometric parameters $\psi$ and $\Delta$ by using the prefixed three optical intensities Ia to Ic. That is, variations in measurement precision due to measurement targets and measurement conditions can be reduced, and stable measurement precision can be maintained.

The respective optical parts shown in FIG. 1 are fixed to, e.g., a base, and no movable portions are present. That is, a measurement time per measurement point can be regarded as the sum of only a conversion time by the A/D converter 11 and a processing time by the personal computer 12, and is about 100 $\mu$sec, which allows measurement almost in real time. Therefore, even if a measurement target moves at high speed, the film thickness d can be accurately measured.

Figure 5:
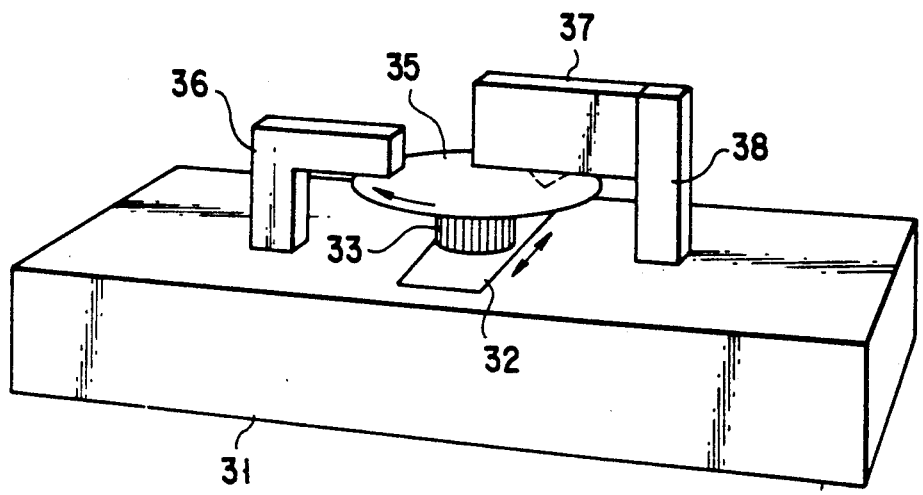
FIG. 5 is a schematic view showing the arrangement of an apparatus for measuring oxide film thicknesses on silicon wafers using the ellipsometer of the embodiment of FIG. 1.
Figure 6:
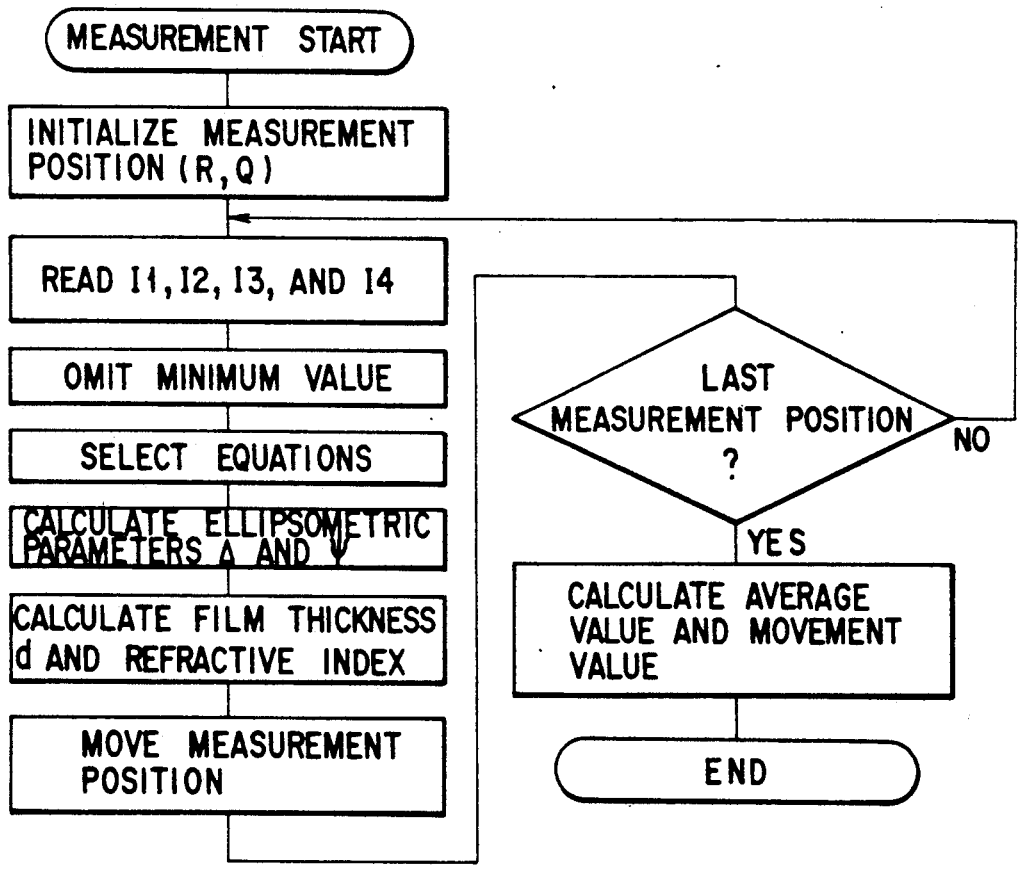
FIG. 6 is a flow chart showing an operation of the oxide film thickness measuring apparatus.

FIG. 5 shows a situation wherein the ellipsometer of the present invention is incorporated in an apparatus for measuring the distribution of oxide film thickness on a silicon wafer.

A moving table 32 is arranged on a base 31. A rotating support base 33 is mounted on the moving table 32. A silicon wafer 35 as a measurement target is attached to the rotating support base 33 by e.g., a suction mechanism. With this arrangement, the silicon wafer 35 is rotated and linearly moved in directions indicated by arrows in FIG. 5. A known thickness measuring unit 36 for measuring the overall thickness of the silicon wafer 35 is arranged on the base 31. In addition, an ellipsometer main body 37 is fixed on the base 31 by a support member 38 to oppose the thickness measuring unit 36.

The thickness measuring unit 36 and the ellipsometer main body 37 respectively measure the overall thickness of the silicon wafer 35 and the thickness d of the oxide film at each measurement position (R,$\theta$) of the silicon wafer 35, which is spirally moved by the moving table 32 and the rotating support base 33.

FIG. 7 is a block diagram showing the electrical arrangement of the apparatus for measuring the distribution of oxide film thickness. The analog optical intensities I1, I2, I3, and I4 output from the light-receiving units 23a, 23b, 23c, and 23d incorporated in the ellipsometer main body 37 are respectively amplified at a predetermined gain by amplifiers 60a, 60b, 60c, and 60d. The amplified data are then sampled/held by sample/-hold (S/H) circuits 61a, 61b, 61c, and 61d for a predetermined period of time. Each sampled/held optical intensity is input to a multiplexer circuit 62. The multiplexer circuit 62 converts the four input optical intensities I1 to I4 into one time division multiplex signal upon time division processing and supplies it to an A/D converter 63. The A/D converter 63 converts the analog time division multiplex signal into a digital data signal and supplies it to a bus line 64.

A CPU (central processing unit) 65 for performing various arithmetic operations and control is connected to the bus line 64. The CPU 65 controls a ROM 66, a data memory 67, an output unit 68, and the like through the bus line 64. The ROM 66 stores control programs. The data memory 67 comprises a RAM for storing various variable data such as the input digital optical intensities I1 to I4. The output unit 68 serves to output an operation result to a display unit or a printer.

In addition, the CPU 65 controls the sample/hold timings of the sample/hold circuits 61a to 61d, and controls the operation of the multiplexer circuit 62. Furthermore, the CPU 65 supplies control signals to a moving mechanism 69 for driving the moving table 32 and the rotating support base 33, thus controlling the moving positions of the moving table 32 and the rotating support base 33.

When a measurement start command is externally input, the CPU 64 executes measurement processing for the film thickness d on the silicon wafer 35 in accordance with the flow chart shown in FIG. 4. In the first step of the flow chart, a control signal is supplied to the moving mechanism 69 to initialize the measurement position (R,θ) on the silicon wafer 35. Thereafter, the optical intensities I1 to I4 at the measurement position are read through the A/D converter 63 and are temporarily written in the data memory 67. The minimum optical intensity of the four read optical intensities I1 to I4 is omitted. Of the above-described conditions A to D, one with which the remaining three optical intensities coincide is retrieved.

Subsequently, the equations designated by the retrieved condition are selected to calculate the ellipsometric parameters ψ and Δ. When the ellipsometric parameters ψ and Δ are obtained, the film thickness d and a refractive index at the measurement position (R,θ) on the silicon wafer 35 are calculated by using other equations. Upon completion of measurement of the film thickness d and the refractive index at one measurement position, the CPU 65 supplies a control signal to the moving mechanism 69 to move the measurement position (R,θ) and execute measurement again. When measurement processing at all the measurement positions is completed, measurement of the single silicon wafer 35 is completed.

Figure 8A:
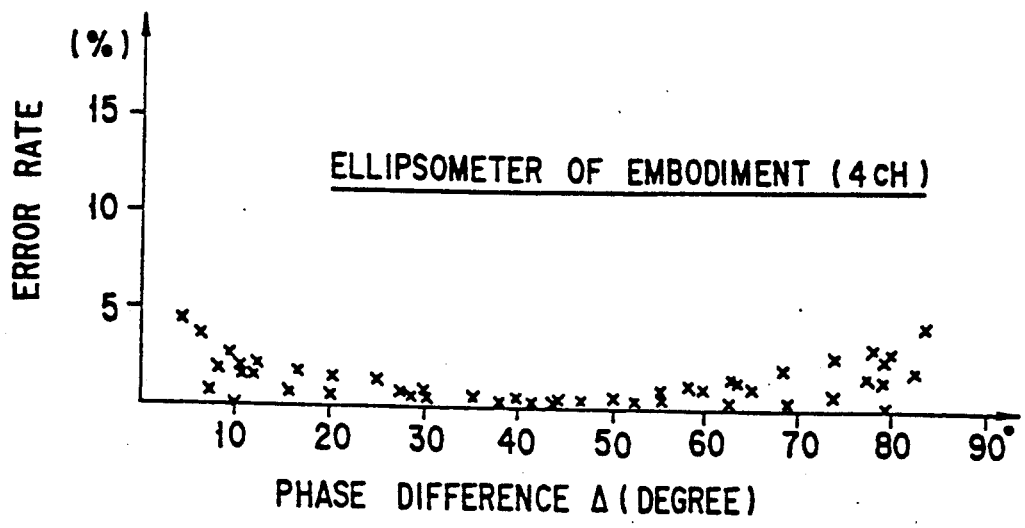
FIGS. 8(a) and 8(b) are views showing measured values for comparing the error rate of the ellipsometer of the present invention using the oxide film thickness measuring apparatus with that of the conventional ellipsometer.
Figure 8B:
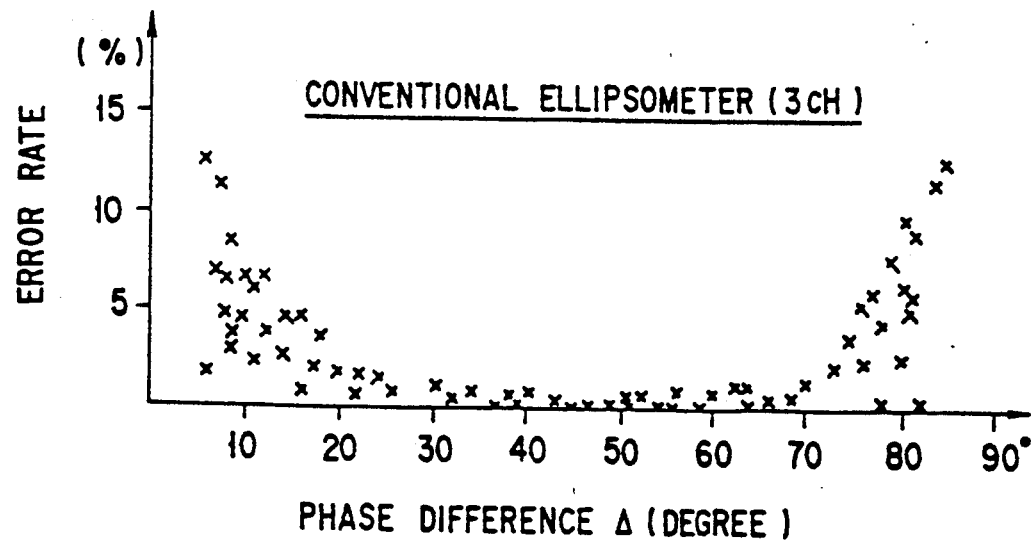

FIGS. 8(a) and 8(b) are graphs, each showing the relationship between the phase differences A as ellipsometric parameters, which are calculated in the execution of film thickness measurement of a large number of silicon wafers 35 having various film thicknesses d, and error rates (%) with respect to the phase differences Δ. FIG. 8(a) shows the result of an experiment using the ellipsometer of the invention. FIG. 8(b) shows the result of an experiment using the conventional ellipsometer.

As shown in FIG. 8(b), in the conventional ellipsometer, errors occur at high rates, up to 10 to 12%, near positions where the phase differences Δ are 0° and 90°, at which one of the three optical intensities Ia to Ic is greatly reduced in value.

In contrast to this, as shown in FIG. 8(a), in the ellipsometer of the invention, since one of the four optical intensities I1 to I4 which is extremely small in value is omitted as described above, the error rate can be reduced to 3 to 5% even near the positions where the phase differences Δ are 0° and 90°.

As described above, since the size of the ellipsometer is reduced while its processing speed is kept high, and an increase in measurement precision is achieved, the ellipsometer can be additionally arranged with the known thickness measuring unit 36. With regard to a semiconductor process line, the ellipsometer of the invention can be applied to on-line measurement of nitride films, polysilicon films, transparent electrode members, and the like other than the above-mentioned silicon wafers.

FIG. 9 shows the schematic arrangement of an ellipsometer according to another embodiment of the present invention. The same reference numerals in FIG. 9 denote the same parts as in FIG. 1, and a repetitive description will be avoided.

In this embodiment, a reflected beam 20a from a non-polarizing beam splitter 19 is split into light components polarized in directions at +45° and −45° with respect to a reference direction by a first polarizing beam splitter 21, whereas a transmitted beam 20b from the non-polarizing beam splitter 19 is split into light components polarized in directions at 90° and 0° with respect to the reference direction by a second polarizing beam splitter 22. In this embodiment, light-receiving units 23c and 23d respectively output optical intensities I1 and I2, and light-receiving units 23a and 23b respectively output optical intensities I3 and I4. Even in such an arrangement, similar to the one shown in FIG. 1, since the optical intensities of the four polarized light components in the respective directions, sequentially shifted from the reference direction by 45°, can be obtained from a reflected beam 18 from a sample surface 13, substantially the same effects as those of the above-described embodiment can be obtained.

FIG. 10 shows an embodiment in which a λ/4 plate 40 is inserted in the optical path of an incident beam 17 radiated from a light source section 16 onto the sample surface 13 in the ellipsometer in FIG. 1. By inserting the λ/4 plate 40 in this manner, the incident beam 17 onto the sample surface 13 can be converted from a linearly polarized beam into a circularly polarized beam. Therefore, the measurement range of film thickness d can be shifted from that of the ellipsometer shown in FIG. 1.

Figure 11:
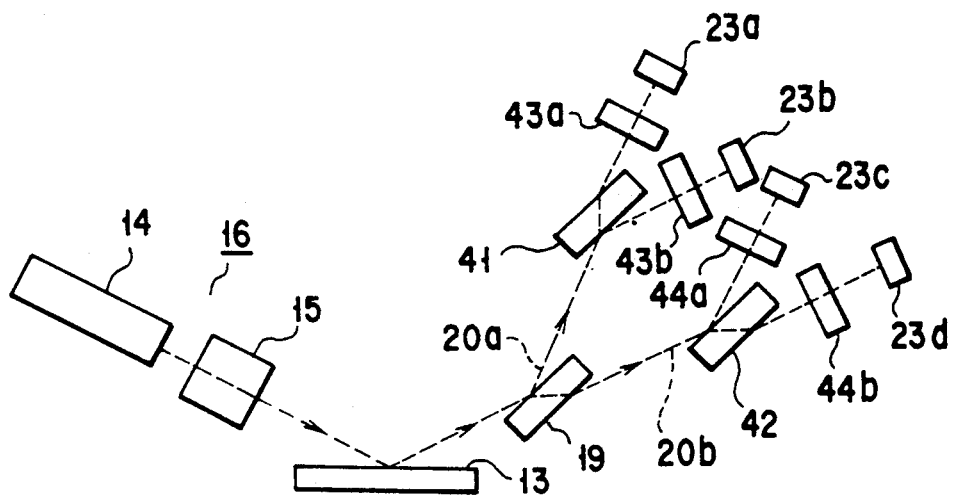
FIG. 11 is a view showing the structure of an ellipsometer according to still another embodiment of the invention.

FIG. 11 shows an embodiment in which a first optical system for dividing a reflected beam 20a, reflected by a non-polarizing beam splitter 19, into polarized light components in different directions comprises a first non-polarizing beam splitter 41, an analyzer 43a for extracting a light component, of a reflected beam from the first non-polarizing beam splitter 41, which is polarized in a direction at 90° with respect to the reference direction, and an analyzer 43b for extracting a light component, of a transmitted beam from the first non-polarizing beam splitter 41, which is polarized in a direction at 0°.

In addition, a second optical system for dividing a transmitted beam 20b, transmitted through the non-polarizing beam splitter 19, into polarized light components in different directions is constituted by a second non-polarizing beam splitter 42, an analyzer 45a for extracting a light component, of a reflected beam from the second non-polarizing beam splitter 42, which is polarized in a direction at +45°, and an analyzer 44b for extracting a light component, of a transmitted beam from the second non-polarizing beam splitter 42, which is polarized in a direction at −45°.

Even if optical systems formed by combining non-polarizing beam splitters and analyzers are used in this manner in place of the polarizing beam splitters 21 and 22, the same effects as those of the embodiment shown in FIG. 1 can be obtained, although the equations for calculating the ellipsometric parameters Δ and ψ must be slightly modified.

Figure 12:
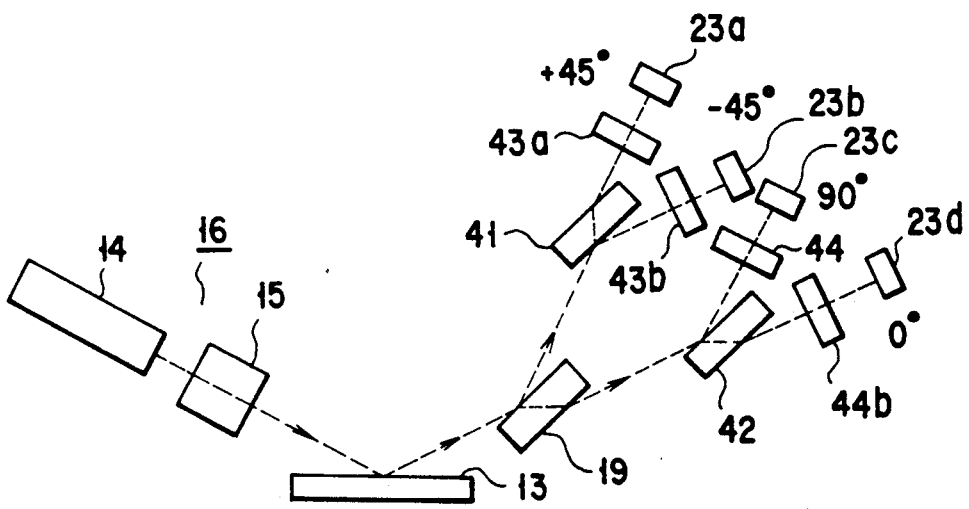
FIG. 12 is a view showing the structure of an ellipsometer according to still another embodiment of the invention.

FIG. 12 shows an embodiment in which the polarization directions of the analyzers 43a and 43b corresponding to the first non-polarizing beam splitter 41 in the embodiment shown in FIG. 11 are respectively set at angles of +45° and −45°, and the polarization directions of the analyzers 44a and 44b corresponding to the second non-polarizing beam splitter 42 are respectively set at angles of 90° and 0°. Even with such an arrangement, substantially the same effects as those of the embodiment shown in FIG. 11 can be obtained.

Figure 13:
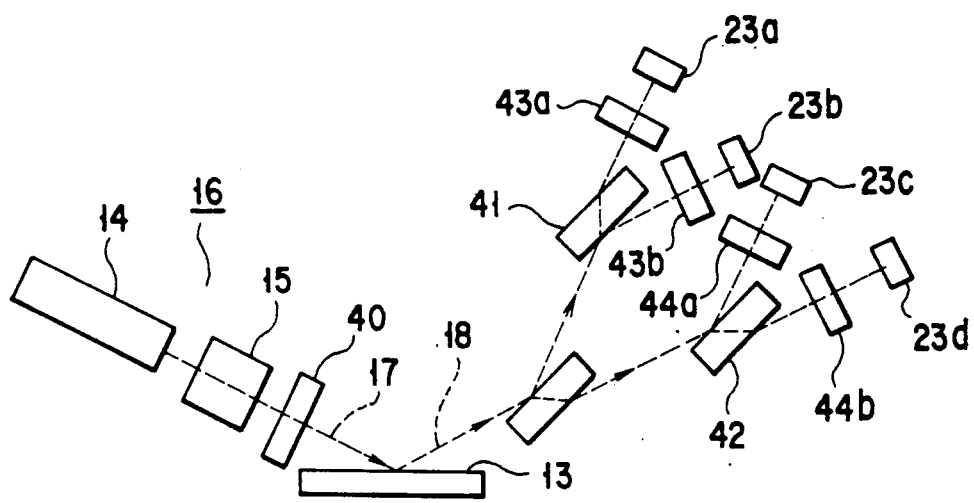
FIG. 13 is a view showing the structure of an ellipsometer according to still another embodiment of the invention.

FIG. 13 shows an embodiment in which, similar to the embodiment shown in FIG. 10, a λ/4 plate 40 is inserted in the optical path of an incident beam 17, radiated from a light source section 16 onto a sample surface 13 in the embodiment shown in FIG. 11. Therefore, substantially the same effects as those of the embodiment in FIG. 10 can be obtained.

FIG. 14 shows the schematic arrangement of an ellipsometer according to still another embodiment of the present invention. The same reference numerals in FIG. 14 denote the same parts as in FIG. 1, and a repetitive description will be avoided.

A reflected beam 18 from a sample surface 13 is split into a reflected beam 20a and a transmitted beam 20b by a non-polarizing beam splitter 19. The reflected beam 20a is incident on an analyzer 45. The analyzer 45 extracts a light component, of the reflected beam 20a, which is polarized in a direction at 0°, and causes it to be incident on a light-receiving unit 23b. The light-receiving unit 23b outputs an optical intensity I2 of the light component polarized in the direction at 0°. The transmitted beam 20b from the non-polarizing beam splitter 19 is incident on the incident surface of a non-polarizing glass member 46.

The non-polarizing glass member 46 comprises, e.g., a prism having a triangular cross-section. The incident surface of a polarizing beam splitter 47 is bonded to the exit surface of the non-polarizing glass member 46 on the opposite side to its incident surface. The angle at which the non-polarizing glass member 46 is mounted is set such that the transmitted beam 20b is incident on the incident surface at the Brewster angle $\theta$. As is known, a beam incident at the Brewster angle $\theta$ is divided into a reflected beam 46a reflected by the incident surface and a transmitted beam 46b transmitted through the incident surface. The reflected beam 46a is constituted by only a light component polarized in a direction parallel to the incident surface (reflection surface), i.e., in a direction at 90° with respect to the reference direction. Therefore, an optical intensity I1 of the reflected beam 46a is detected by a light receiving unit 23a.

The transmitted beam 46b, which is transmitted through the non-polarizing glass member 46 while its elliptical polarization state is maintained, is incident on the polarizing beam splitter 47 through the exit surface on the side opposite to the incident surface. In this case, the sectional shape of the non-polarizing glass member 46 is set such that the transmitted beam 46b emerges at a right angle with respect to the exit surface. The angular position of the polarizing beam splitter 47 around the optical axis is set such that the transmitted beam 46b incident thereon is split into light components polarized in directions at +45° and −45° with respect to the reference direction. An optical intensity I3 of the light component polarized in the direction at +45° is detected by a light-receiving unit 23c. An optical intensity I4 of the light component polarized in the direction at −45° is detected by a light-receiving unit 23d.

With this arrangement, the optical intensities I1 to I4 of the light components, of the reflected beam 18 reflected by the sample surface 13 and having the elliptically polarized beam, which are respectively polarized in directions at 90°, 0°, +45°, and −45° are obtained by the light-receiving units 23a to 23d. Therefore, substantially the same effects as those of the embodiment shown in FIG. 1 can be obtained, although the equations for calculating the ellipsometric parameters $\Delta$ and $\psi$ must be slightly modified because different optical systems are used.

FIG. 15 shows the schematic arrangement of an ellipsometer according to still another embodiment of the present invention. The same reference numerals in FIG. 15 denote the same parts as in FIG. 1, and a repetitive description will be omitted.

In this embodiment, a reflected beam 18 having an elliptically polarized beam and reflected by a sample surface 13 is incident on a composite beam splitter 48. The composite beam splitter 48 comprises, as one optical part, a non-polarizing glass member 49 having a four-cornered sectional shape, a first polarizing beam splitter 50, and a second polarizing beam splitter 51. Part of the incident surface of the first polarizing beam splitter 50 is fixed to the upper surface of the non-polarizing glass member 49 with, e.g., an adhesive agent. The incident surface of the second polarizing beam splitter 51 is bonded to the exit surface of the non-polarizing glass member 49.

The reflected beam 18 from the sample surface is divided into a reflected beam 49a and a transmitted beam 49b at the incident surface of the non-polarizing glass member 49 while its elliptical polarization state is maintained. Note that an incident angle $\theta$ is deliberately set to be an angle other than the Brewster angle $\theta$. The reflected beam 49a from the non-polarizing glass member 49 is perpendicularly incident on the incident surface of the first polarizing beam splitter 50. Meanwhile, the transmitted beam 49b is transmitted through the non-polarizing glass member 49 and is perpendicularly incident on the incident surface of the second polarizing beam splitter 51. That is, the installation of the composite beam splitter 48 with respect to the reflected beam 18, and the angle of the incident surface of the non-polarizing glass member 49 are adjusted such that the reflected beam 49a and the transmitted beam 49b are perpendicularly incident on the incident surfaces of the first and second polarizing beam splitters 50 and 51, respectively.

The first polarizing beam splitter 50 splits the reflected beam 49a into a transmitted beam having a light component polarized in a direction at 90° with respect to the reference direction, and a reflected beam having a light component polarized in a direction at 0° with respect to the reference direction, and causes them to be incident on light-receiving units 23a and 23b, respectively. Similarly, the second polarizing beam splitter 51 splits the transmitted beam 41b, transmitted through the non-polarizing glass member 49, into a transmitted beam having a light component polarized in a direction at 45° with respect to the reference direction and a reflected beam having a light component polarized at −45° with respect to the reference direction, and causes them to be incident on light-receiving units 23c and 23d, respectively.

With this arrangement, optical intensities I1 to I4 obtained by the light-receiving units 23a to 23d respectively coincide with the optical intensities of the light components, of the elliptically polarized beam of the reflected beam 18 from the sample surface 13, which are polarized in the directions at 90°, 0°, 45°, and −45°. Similar to the embodiment shown in FIG. 1, ellipsometric parameters $\psi$ and $\Delta$ defining the elliptically polarized beam shown in FIG. 2 are calculated by using three of the four optical intensities I1 to I4 obtained by the light-receiving units 23a to 23d, which have larger values than the remaining one. Therefore, substantially the same effects as those of the embodiment shown in FIG. 1 can be obtained.

Furthermore, in this embodiment, a plurality of optical elements for dividing the reflected beam 18, reflected by the sample surface 13 into four different polarized light components are bonded to each other with, e.g., an adhesive agent to constitute one optical part. Therefore, in the manufacture of this ellipsometer, assembly and adjustment can be greatly simplified. In addition, since the number of parts is small, inspection/maintenance operations can be simplified in a long-term operation period. Moreover, the overall apparatus can be reduced in size and weight.

Figure 16:
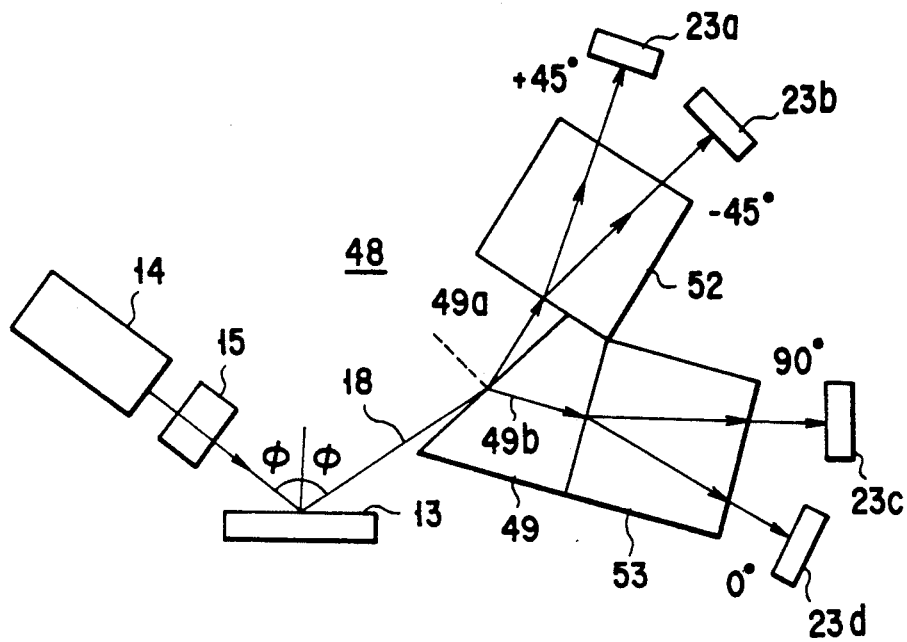
FIG. 16 is a view showing the structure of another embodiment using a composite beam splitter.

FIG. 16 shows an embodiment in which the installation angle of each polarizing beam splitter around the optical axis is changed to change the polarization direction of a polarized light component extracted from each polarizing beam splitter in the embodiment shown in FIG. 15.

More specifically, in this embodiment, the polarization directions of polarized light components extracted from a first polarizing beam splitter 52 are set at angles of $+45°$ and $-45°$ with respect to the reference direction. The polarization directions of polarized light components extracted from a second polarizing beam splitter 53 are set at angles of $90°$ and $0°$ with respect to the reference direction.

In the ellipsometer having the above-described arrangement, since optical intensities I1 to I4 of beams polarized in directions shifted from each other by $45°$ are obtained, substantially the same effects as those of the embodiment shown in FIG. 15 can be obtained.

Figure 17:
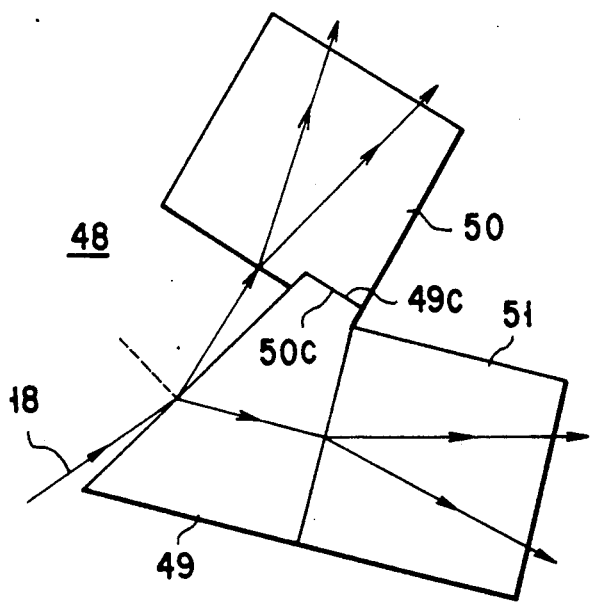
FIG. 17 is a view showing the structure of the composite beam splitter in detail.

FIG. 17 is a detailed illustration of the joining portion between a non-polarizing glass member 49 and a first polarizing beam splitter 50 in a composite beam splitter 48 according to still another embodiment of the present invention. In this embodiment, a stepped portion 50c is formed on part of the incident surface of the first polarizing beam splitter 50 such that an upper surface 49c of the non-polarizing glass member 49 is fitted in the stepped portion 50c. By forming such an engaging portion, alignment with the optical axis can be more accurately performed, and the composite beam splitter 48 can be formed firmly. As described above, the present invention can be carried out by variously combining optical parts.

As has been described above, according to the measuring method for ellipsometric parameters and the ellipsometer of the present invention, a reflected beam having an elliptically polarized beam reflected by a measurement target is divided into four light components polarized in different directions, and the optical intensities of the respective polarized light components are detected. Of the four detected optical intensities, one having the minimum value is omitted, and ellipsometric parameters are calculated by using the remaining three optical intensities having large values. In addition, the ellipsometer is constituted by only stationary optical parts without using any movable optical parts. Therefore, film thickness measurement precision higher than a certain level can always be achieved together with high measurement speed.

In addition, since no movable portions are present, inspection/maintenance operations can be simplified. Moreover, by using a composite beam splitter, the overall apparatus can be further reduced in size and weight.

We claim:

1. An ellipsometer comprising:
 a light source section for radiating a polarized light beam onto a measurement target at a predetermined angle;
 a non-polarizing beam splitter for receiving a reflected light beam from the measurement target and for splitting the received reflected light beam into two split light beams of different directions;
 a plurality of optical members for dividing each of said split light beams into two light beams having different polarization directions, whereby the received reflected light beam, reflected by the measurement target, is divided into four different polarized light components;
 four light-receiving units for detecting light intensities of the respective four different polarized light components; and
 means for selecting the three polarized light components having the three highest light intensities out of the four light intensities detected by said four light-receiving units; and
 means for calculating ellipsometric parameters of an elliptically polarized beam of the reflected beam on the basis of the three selected polarized light components having said three highest light intensities.

2. The ellipsometer of claim 1, wherein said plurality of optical members comprises:
 a first optical system for dividing one of said split light beams into light components respectively polarized in directions at $+90°$ and $0°$ with respect to a reference direction; and
 a second optical system for dividing the other of said split light beams into light components respectively polarized in directions at $+45''$ and $-45''$ with respect to said reference direction.

3. The ellipsometer of claim 2, further comprising a wave plate inserted in one of optical paths of incident and reflected beams with respect to the measurement target.

4. The ellipsometer of claim 3, wherein said wave plate is a $\lambda/4$ wave plate.

5. The ellipsometer of claim 1, further comprising a wave plate inserted in one of optical paths of incident and reflected beams with respect to the measurement target.

6. The ellipsometer of claim 5, wherein said wave plate is a $\lambda/4$ wave plate.

7. An ellipsometer comprising:
 a light source section for radiating a polarized light beam onto a measurement target at a predetermined angle;
 a composite beam splitter for splitting a reflected light beam from the measurement target into four different polarized light components, each of which has a respective light intensity;
 four light-receiving units for detecting the light intensities of the four respective polarized light components produced by said composite beam splitter;
 means for selecting three of said polarized light components having the three highest light intensities out of the four light intensities detected by said four light-receiving units; and
 means for calculating ellipsometric parameters of an elliptically polarized light beam of the reflected light beam on the basis of the three selected polarized light components having said three highest light intensities,
 said composite beam splitter comprising:

a non-polarizing member for splitting the reflected light beam from the measurement target, at an incident surface of said non-polarizing member, into a reflected light beam and a transmitted light beam;

a first polarizing beam splitter, having one end fixed to said non-polarizing member, for splitting the reflected light beam from said non-polarizing member into light components polarized in directions at +90° and 0° with respect to a reference direction; and a second polarizing beam splitter, bonded to an exit surface of said non-polarizing member, from which the transmitted light beam emerges, for splitting the transmitted light beam from said non-polarizing member into light components polarized in directions at +45° and −45° with respect to said reference direction.

8. The ellipsometer of claim 7, wherein said non-polarizing member comprises a glass member.

9. An ellipsometer comprising:

a light source section for radiating a polarized light beam onto a measurement target at a predetermined angle;

a composite beam splitter for splitting a reflected light beam from the measurement target into four different polarized light components, each of which has a respective light intensity;

four light-receiving units for detecting the light intensities of the four respective polarized light components produced by said composite beam splitter;

means for selecting three of said polarized light components having the three highest light intensities out of the four light intensities detected by said four light-receiving units; and means for calculating ellipsometric parameters of an elliptically polarized light beam of the reflected light beam on the basis of the three selected polarized light components having said three highest light intensities, said composite beam splitter comprising:

a non-polarizing member for splitting the reflected light beam from the measurement target, at an incident surface of said non-polarizing member, into a reflected light beam and a transmitted light beam;

a first polarizing beam splitter, having one end fixed to said non-polarizing member, for splitting the reflected light beam from said non-polarizing member into light components polarized in directions at +45° and −45° with respect to a reference direction; and a second polarizing beam splitter, bonded to an exit surface of said non-polarizing member, from which the transmitted beam emerges, for splitting the transmitted light beam from said non-polarizing member into light components polarized in directions at +90° and 0° with respect to said reference direction.

10. The ellipsometer of claim 9, wherein said non-polarizing member comprises a glass member.

* * * * *